(12) United States Patent
Cheng et al.

(10) Patent No.: US 8,778,395 B2
(45) Date of Patent: Jul. 15, 2014

(54) DILTIAZEM CONTROLLED RELEASE FORMULATION AND METHOD OF MANUFACTURE

(75) Inventors: Xiu Xiu Cheng, Weston, FL (US); Xiaohong Qi, Dave, FL (US); Guohua Zhang, Parsippany, NJ (US); Manesh Dixit, Sunrise, FL (US)

(73) Assignee: Andrx Labs, LLC, Davie, FL (US)

( * ) Notice: Subject to any disclaimer, the term of this patent is extended or adjusted under 35 U.S.C. 154(b) by 1518 days.

(21) Appl. No.: 11/201,747

(22) Filed: Aug. 11, 2005

(65) Prior Publication Data
US 2007/0036856 A1 Feb. 15, 2007

(51) Int. Cl.
A61K 9/26 (2006.01)
A61K 31/554 (2006.01)

(52) U.S. Cl.
USPC ........................................ 424/469; 514/211.07

(58) Field of Classification Search
None
See application file for complete search history.

(56) References Cited

U.S. PATENT DOCUMENTS

| | | |
|---|---|---|
| 2,798,053 A | 7/1957 | Brown |
| 2,909,462 A | 10/1959 | Warfield et al. |
| 4,207,893 A | 6/1980 | Michaels |
| 4,327,725 A | 5/1982 | Cortese et al. |
| 4,404,183 A | 9/1983 | Kawata et al. |
| 4,434,153 A | 2/1984 | Urquhar et al. |
| 4,824,675 A | 4/1989 | Wong et al. |
| 4,839,177 A | 6/1989 | Colombo et al. |
| 4,851,232 A * | 7/1989 | Urquhart et al. ............. 424/469 |
| 4,876,093 A | 10/1989 | Theeuwes et al. |
| 4,892,778 A | 1/1990 | Theeuwes et al. |
| 4,894,240 A | 1/1990 | Geoghegan et al. |
| 4,915,949 A | 4/1990 | Wong et al. |
| 4,940,465 A | 7/1990 | Theeuwes et al. |
| 4,992,278 A | 2/1991 | Khanna |
| 5,002,776 A | 3/1991 | Geoghegan et al. |
| 5,007,790 A | 4/1991 | Shell |
| 5,035,897 A | 7/1991 | Ayer et al. |
| 5,075,114 A | 12/1991 | Roche |
| 5,082,668 A | 1/1992 | Wong et al. |
| 5,120,548 A | 6/1992 | McClelland et al. |
| 5,156,850 A | 10/1992 | Wong et al. |
| 5,190,765 A | 3/1993 | Jao et al. |
| 5,232,705 A | 8/1993 | Wong et al. |
| 5,252,338 A | 10/1993 | Jao et al. |
| 5,254,349 A | 10/1993 | Dong et al. |

(Continued)

FOREIGN PATENT DOCUMENTS

| | | |
|---|---|---|
| EP | 332 392 | 6/1989 |
| WO | WO 93/18755 | 9/1993 |

(Continued)

OTHER PUBLICATIONS

Sood et al. Use of Extrusion-Spheronization to Develop Controlled Release Dosage Forms for Diltiazem Hydrochloride. Apr. 2004.*

(Continued)

*Primary Examiner* — Scott Long
*Assistant Examiner* — Sarah Alawadi
(74) *Attorney, Agent, or Firm* — Florek & Endres PLLC

(57) ABSTRACT

A controlled release diltiazem dosage formulation comprising a plurality of diltiazem pellets and a gel-forming material where the time of maximum diltiazem blood plasma levels occurs more than 8 hours after administration and preferably more than 10 hours after administration.

5 Claims, 6 Drawing Sheets

(56) References Cited

U.S. PATENT DOCUMENTS

| | | |
|---|---|---|
| 5,273,758 A | 12/1993 | Royce |
| 5,286,497 A | 2/1994 | Hendrickson et al. |
| 5,288,505 A | 2/1994 | Deboeck et al. |
| 5,344,657 A | 9/1994 | Desmolin |
| 5,364,620 A | 11/1994 | Geoghegan et al. |
| 5,370,879 A | 12/1994 | Masterson et al. |
| 5,417,985 A | 5/1995 | Coutel et al. |
| 5,419,917 A | 5/1995 | Chen et al. |
| 5,422,123 A | 6/1995 | Conte et al. |
| 5,439,689 A | 8/1995 | Hendrickson et al. |
| 5,470,584 A | 11/1995 | Hendrickson et al. |
| 5,472,710 A | 12/1995 | Klokkers-Bethke et al. |
| 5,508,040 A | 4/1996 | Chen |
| 5,529,791 A | 6/1996 | Deboeck et al. |
| 5,536,508 A | 7/1996 | Canal et al. |
| 5,545,423 A | 8/1996 | Soon-Shiong et al. |
| 5,567,441 A | 10/1996 | Chen |
| 5,582,838 A | 12/1996 | Rork et al. |
| 5,676,972 A | 10/1997 | Galiatsatos et al. |
| 5,716,981 A | 2/1998 | Hunter et al. |
| 5,766,623 A | 6/1998 | Ayres et al. |
| 5,785,994 A | 7/1998 | Wong et al. |
| 5,830,503 A | 11/1998 | Chen |
| 5,834,024 A * | 11/1998 | Heinicke et al. ............... 424/497 |
| 5,840,329 A | 11/1998 | Bai |
| 5,840,332 A | 11/1998 | Lerner et al. |
| 5,908,638 A | 6/1999 | Huber et al. |
| 5,922,352 A | 7/1999 | Chen et al. |
| 5,945,125 A | 8/1999 | Kim |
| 5,962,477 A | 10/1999 | Mak |
| 5,972,389 A | 10/1999 | Shell et al. |
| 6,024,982 A | 2/2000 | Oshlack et al. |
| 6,046,177 A | 4/2000 | Stella et al. |
| 6,048,547 A | 4/2000 | Seth et al. |
| 6,068,854 A | 5/2000 | Wunderlich et al. |
| 6,096,339 A | 8/2000 | Ayer et al. |
| 6,117,453 A | 9/2000 | Seth et al. |
| 6,120,803 A | 9/2000 | Wong et al. |
| 6,146,662 A | 11/2000 | Jao et al. |
| 6,228,395 B1 | 5/2001 | DeBregeas et al. |
| 6,228,398 B1 | 5/2001 | Devane et al. |
| 6,270,805 B1 | 8/2001 | Chen et al. |
| 6,287,599 B1 | 9/2001 | Burnside et al. |
| 6,337,091 B1 | 1/2002 | Kim et al. |
| 6,340,475 B2 | 1/2002 | Shell et al. |
| 6,342,250 B1 | 1/2002 | Masters |
| 6,368,628 B1 | 4/2002 | Seth |
| 6,419,954 B1 * | 7/2002 | Chu et al. ................ 424/465 |
| 6,488,962 B1 | 12/2002 | Berner et al. |
| 6,524,620 B2 * | 2/2003 | Chen et al. ................ 424/490 |
| 6,531,152 B1 | 3/2003 | Lerner et al. |
| 6,548,083 B1 | 4/2003 | Wong et al. |
| 6,620,439 B1 | 9/2003 | Metha |
| 6,632,451 B2 | 10/2003 | Penhasi et al. |
| 6,635,280 B2 | 10/2003 | Shell et al. |
| 6,673,369 B2 | 1/2004 | Rampal et al. |
| 6,753,011 B2 | 6/2004 | Faour |
| 6,761,895 B2 | 7/2004 | Sawada et al. |
| 6,923,984 B1 | 8/2005 | Remon |
| 6,926,909 B2 | 8/2005 | Mehta |
| 2003/0108602 A1 | 6/2003 | Chu et al. |
| 2004/0037883 A1 | 2/2004 | Zhou et al. |
| 2004/0176352 A1 | 9/2004 | Albert et al. |
| 2006/0062851 A1 * | 3/2006 | Vergez et al. ................ 424/473 |
| 2006/0257482 A1 * | 11/2006 | Kumar et al. ................ 424/469 |

FOREIGN PATENT DOCUMENTS

| | | |
|---|---|---|
| WO | WO 95/31186 | 11/1995 |
| WO | WO 97/23219 | 7/1997 |
| WO | WO 98/11879 | 3/1998 |
| WO | WO 00/04883 | 2/2000 |
| WO | WO 01/41744 | 6/2001 |
| WO | WO 02/28376 | 4/2002 |
| WO | WO 02/28376 | 11/2002 |
| WO | WO 2004/091583 | 10/2004 |
| WO | WO 2005/016317 | 2/2005 |

OTHER PUBLICATIONS

Administration-Time-Dependent Effects of Diltiazem on the 24-Hour Blood Pressure Profile of Essential Hypertension Patients, Oct. 1996.

Kohno et al., Chronobiology International, vol. 14, No. 1, pp. 71-84 (1997).

The Influence of Time of Administration on the Pharmacokinetics of Once-A-Day Diltiazem Formulation: Morning Against Bedtime, 1996.

Thiffault et. al., Biopharmaceutics & Drug Disposition, vol. 17, pp. 107-115 (1996).

Recent trends and progress in sustained or controlled oral delivery of some water soluble drugs: Morphine Salts, Diltiazem and Captopril, May 1995.

M. Zahirul, vol. 21, No. 9 pp. 1037-1077 (1995).

Development of a multiple unit drug delivery system for positioned release in the gastrointestinal tract, Aug. 1994.

Klokkers-Bethke vol. 15, No. 2. pp. 105-112 (1991).

Cardizem® LA Product Labeling, Apr. 2004.

Schifferer, Hermann, Supplemental European Search Report, dated Sep. 30, 2010, in EP 06 80 1043, European Patent Office, 80298 Munich, Germany.

* cited by examiner

DILTIAZEM CONTROLLED RELEASE FORMULATION AND METHOD OF MANUFACTURE

BACKGROUND OF THE INVENTION

The present invention relates to a controlled release formulation for the drug diltiazem or its pharmaceutically acceptable salts thereof and a method for manufacturing a controlled release dosage formulation containing diltiazem or a pharmaceutically acceptable salt thereof as the active ingredient. More specifically, the present invention relates to a modified controlled release formulation of diltiazem that is designed to be administered to patients before bedtime and to release the diltiazem in a controlled release manner so that the time of maximum concentration of diltiazem in the patients blood stream occurs in the morning hours when the patient is waking, i.e. more than 8 hours after administration, preferably more than 9 hours after administration, and most preferably between 10 and 15 hours after administration. Such modified controlled release systems that are designed to release the active ingredient at a time when the patient is most in need of the drug has been referred to a "chronotherapy" or "chronotherapeutics" in the art.

Diltiazem hydrochloride, commonly referred to as diltiazem, is a benzothiazine derivative that blocks the influx of calcium ions in smooth and cardiac muscle and has few side effects. Diltiazem has been shown to be useful in alleviating symptoms of chronic heart disease, particularly angina pectoris, myocardial ischemia and hypertension. Diltiazem also has been shown to have activity against arrythmia and may be useful in treating congestive cardiac insufficiency, Raynaud's syndrome and peripheral and cerebral circulatory insufficiency.

Recent publications relating to once a day diltiazem treatments have indicated that the time of the day (i.e. morning or evening) at which a patient takes the medication can affect the patients response to the medication. See generally *Administration-Time-Dependent Effects of Diltiazem on the 24-Hour Blood Pressure Profile of Essential Hypertension Patients*, by Kohno et al., Chronobiology International, Vol. 14, No. 1, pp. 71-84 (1997) and *The Influence of Time of Administration on the Pharmacokinetics of Once-A-Day Diltiazem Formulation: Morning Against Bedtime*, by Thiffault et al., Biopharmaceutics & Drug Disposition, Vol. 17, pp. 107-115 (1996). These publications suggest that an administration schedule that allows the maximum amount of diltiazem in the patients blood stream to occur in the morning hours, i.e. between 7:00 AM and 11:00 AM is the optimum dosing schedule.

Diltiazem is sold commercially in extended release pharmaceutical dosage forms that attempt to maintain a therapeutic serum level of diltiazem and minimize the effects of missed doses of the drug caused by lack of patient compliance. Some of the commercial forms currently available are CARDIZEM CD®, CARTIA®, CARDIZEM LA®, TIAZAC®, TAZTIA®, and DILACOR XR®. The FDA's Approved Drug Products with Therapeutic Equivalents publication, commonly known as the "Orange Book" lists the following patents for some of the aforementioned extended release dosage forms of diltiazem: U.S. Pat. Nos. 4,894,240; 5,470,584; 5,439,689; 5,286,497; 5,364,620; 5,002,776; 5,529,791; 5,288,505; 4,839,177 and 5,422,123. Other patents that describe extended release forms of diltiazem and that are owned by the assignee of the present application are U.S. Pat. Nos. 5,508,040; 5,419,917; 5,567,441; 6,524,620 and 6,270,805. These products typically release the drug so the maximum blood concentration occurs about eight to eleven hours after administration.

CARDIZEM® LA is a commercially available form of chronotherapeutic diltiazem which has recently become available. It is believed that this product is described in WO 01/41744. The formulations described in the CARDIZEM® LA labeling and in WO 01/41744 appear to employ free diltiazem (not coated) and diltiazem beads (extended release coated diltiazem pellets) that are mixed with a hydrophobic or wax material to control the release of the diltiazem from the dosage form. This dosage form is complicated and difficult to manufacturer.

It is an object of the present invention to provide a novel once-a-day chronotherapeutic form of diltiazem formulation that is easy to manufacture and provides a maximum concentration of diltiazem in the patients blood system at a time greater than 8 hours, preferably greater than 9 hours, most preferably between 10 and 15 hours, after administration.

SUMMARY OF THE INVENTION

The foregoing objectives are met by the present invention that is directed to a modified controlled release or chronotherapeutic pharmaceutical dosage formulation comprising a plurality of diltiazem pellets that are mixed with a gel-forming material. The diltiazem pellets and gel-forming material are compressed into a tablet or placed into a gelatin capsule.

The pellets can be any type of conventionally known pellets that are described in the art such as the pellets described in Examples 1-3 of U.S. Pat. No. 5,470,584, Examples I and II of U.S. Pat. No. 5,508,040, Example 1 of U.S. Pat. No. 5,567,441; Examples 1-21 of U.S. Pat. No. 5,002,776; Example 1 and 2 of U.S. Pat. No. 6,270,805; Examples 1-4 of U.S. Pat. No. 5,529,791 and Examples 1 and 2 of U.S. Pat. No. 6,524,620. Copies of the foregoing patent examples are incorporated herein by reference. In a preferred embodiment, the diltiazem pellets comprise a combination of pellets such as those described in Example 2 of U.S. Pat. No. 5,470,584, Examples 1 and 2 of U.S. Pat. No. 6,270,805 and most preferably as described in Examples 1 and 2 of U.S. Pat. No. 6,524,620.

The gelling material can be any type of material such as those described in Col. 10, line 44 to Col. 11, line 50 of U.S. Pat. No. 4,915,949 and Col. 16, line 14 to Col. 17, line 20 of U.S. Pat. No. 6,419,954 which are incorporated herein by reference.

The dosage formulation of the present invention may contain a homogeneous population of diltiazem wherein each pellet comprises approximately the same amount or thickness of extended release coating. The dosage form of the present invention may also contain a heterogeneous population of diltiazem pellets wherein the population comprises a blend or mixture of diltiazem pellets with different amounts or thicknesses of extended release coating on some of the pellets while some of the pellets may have no controlled release coating. The pellets without a controlled release coating are sometimes referred to herein as active pellets.

A heterogeneous population of diltiazem pellets of the present invention can be obtained in a single batch intermittent coating process and thereby eliminate the need for several separate coating batches and a separate and distinct blending step. The unique process comprises adding a first allotment of active pellets to a coating apparatus; coating the first allotment of active pellets with a first amount of extended release coating; adding a second allotment of active pellets to the coating apparatus after the coating of the first allotment of active pellets with the first amount of extended release coating; and coating the first and second allotment of active pellets with a second amount of extended release coating. Additional allotments, i.e. a third allotment or a fourth allotment, of active pellets may also be added to the coating apparatus at subsequent time periods during the coating process and coating all the allotments of active pellets with additional amounts of extended release coating. Once the coating process is completed a heterogeneous population of pellets is obtained wherein the first allotment of active pellets has the greatest amount of (or thickest) extended release coating, the second allotment of active pellets are coated with less extended release coating than the first allotment, and the third allotment of active pellets, if employed, are coated with less extended release coating than the first and second allotments of active pellets.

Once the diltiazem pellets are prepared, they are mixed with a gel-forming material and pressed into a tablet or filled into a gelation capsule using conventional methods known in the art. The combination of the extended release coating material on the active diltiazem pellets and the amount of gel-forming material should control the release of the diltiazem from the dosage formulation so that the time ($T_{max}$) of the peak blood plasma level ($C_{max}$) of the diltiazem is obtained more than 8 hours after administration, preferably more than 9 hours after administration and most preferably about 10 to about 15 hours after administration.

DETAILED DESCRIPTION OF THE INVENTION

Figure 1:
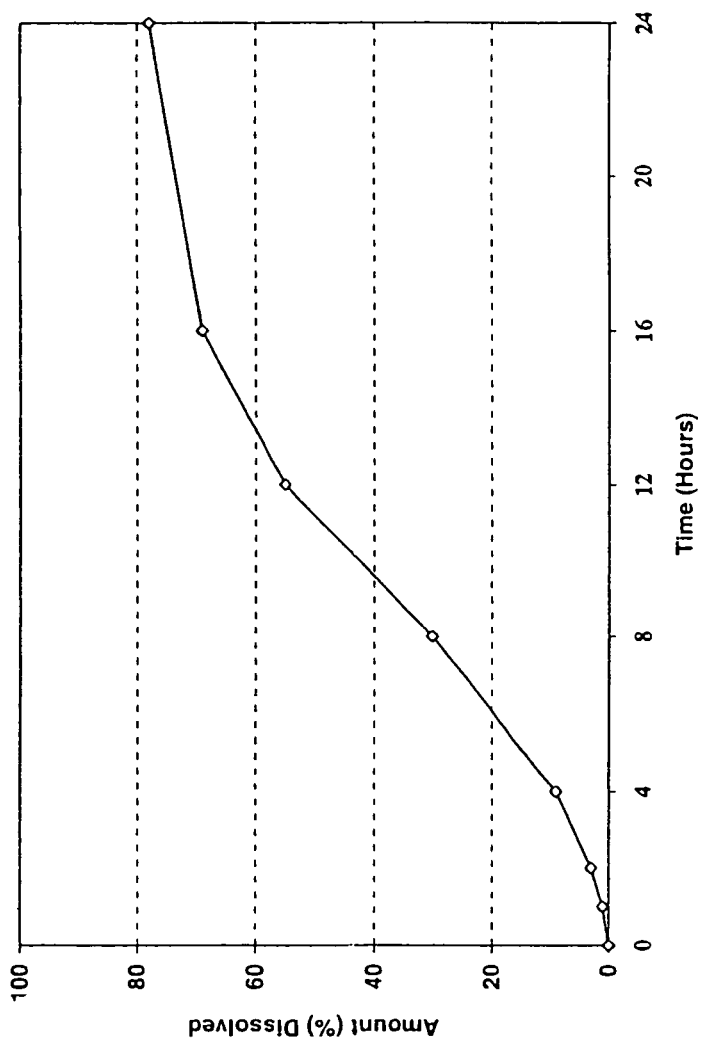
FIG. 1 is a graph depicting the dissolution profile in simulated intestinal fluid (pH 7.5 phosphate buffer) of the formulation described in Example 1 as tested according to the procedure described in United States Pharmacopoeia 25, Apparatus 1 @ 100 rpm.

The present invention is a modified controlled release once a day oral diltiazem formulation that is suitable for night time administration. The formulation comprises a plurality of diltiazem pellets that are mixed with a gel-forming material so that the time ($T_{max}$) of the peak blood plasma level ($C_{max}$) of the diltiazem is more than 8 hours after administration, preferably more than 9 hours after administration and most preferably about 10 to about 15 hours after administration of the dosage formulation. The diltiazem pellets can be a homogeneous population of diltiazem pellets, or a heterogeneous population of pellets.

If the diltiazem pellets are a homogeneous population of pellets, the final dosage form can be coated with a layer of diltiazem to provide an immediate release amount of diltiazem upon ingestion by the patient. If the diltiazem pellets are a heterogeneous population of pellets, the final dosage form can be also be coated with diltiazem to provide an immediate release amount of diltiazem or a population of active or non-coated diltiazem pellets can be employed to provide an immediate release amount of diltiazem.

If a heterogeneous population of diltiazem pellets are employed the heterogeneous population can consist of: (a) a combination of active (i.e. immediate release or non-coated) pellets and extended release coated pellets as disclosed in U.S. Pat. No. 5,002,776; (b) a combination of two types of extended release coated diltiazem pellets, i.e., a "fast" or "enteric" release coated diltiazem pellet and a "slow" or "delayed" release coated pellet as described in Example 2 of U.S. Pat. No. 5,470,584 or Examples 1 and 2 of U.S. Pat. No. 6,270,805, or (c) a combination of three types of extended release coated diltiazem pellets as disclosed in Examples 1 and 2 of U.S. Pat. No. 6,524,620.

The gel-forming material is a material that exhibits the ability to retain a significant fraction of imbibed fluid in the molecular structure. In a preferred embodiment the gel-forming material is a polymer that can swell or expand to a very high degree, usually exhibiting a 2 to 50 fold volume increase. The swellable polymers are also known as osmopolymers or hydrogels and can be non-cross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include polyhydroxyalkylcellulose having a molecular weight greater than 50,000; poly(hydroxyalkylmethacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; water swellable copolymer produced by a dispersion of finely divided copolymer of maleic anhydride with styrene, ethylene, propylene, or isobutylene; water swellable polymer of N-vinyl lactams; and the like.

Other gellable, fluid imbibing and retaining polymers useful in the present invention include pectin having a molecular weight ranging from 30,000 to 300,000; polysaccharides such as agar, acacia, karaya, tragacanth, algins and guar;

CARBOPOL®, an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOLS® 934, 940 and 941, and its salt derivatives; polyacrylamides; water-swellable indene maleic anhydride polymers; GOOD-RITE® polyacrylic acid having a molecular weight of 80,000 to 200,000; POLYOX® polyethylene oxide polymers having a molecular weight of 100,000 to 5,000,000; starch graft copolymers; AQUA-KEEP® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; hydroxypropylcellulose such as METHOCEL K100M and the like. Representative polymers possessing gelling properties are known in U.S. Pat. Nos. 6,419,954; 4,915,949; 4,327,725; 4,207,893 and in *Handbook of Common Polymers*, by Scott and Roff, published by Cleveland Rubber Company, Cleveland, Ohio.

The present invention may also employ a flux enhancer. A flux enhancer is an inorganic or organic compound that exhibits an osmotic pressure gradient against an external fluid, preferably water or gastric fluid, and across a semipermeable membrane. Flux enhancers useful for the present invention include inorganic and organic salts, polysaccharides, carbohydrates, and the like. Representative flux enhancers include magnesium sulfate, magnesium chloride, sodium chloride, potassium chloride, lithium chloride, potassium sulfate, sodium carbonate, sodium sulfate, lithium sulfate, sodium sulfate, potassium acid phosphate, calcium lactate, tartaric acid, lactose, fructose, sucrose, mannitol, sorbitol, and mixtures thereof.

If a flux enhancer is employed it should be blended with the gel-forming material and the diltiazem pellets prior to compressing the material into a tablet or filling the material into a gelatin capsule.

In addition to the diltiazem pellets, gel-forming agent and optional flux enhancer, the dosage form of the present invention may further comprise conventional pharmaceutical excipients of processing aids such as fillers, lubricants, glidants, pigments, polishing agents and combinations of the foregoing.

DETAILED DESCRIPTION OF AN EMBODIMENT OF THE INVENTION

The following is a description of an embodiment of the present invention. Although the following description relates to the preparation of a tablet that contains a three pellet heterogeneous population of diltiazem pellets, the use of a homogeneous population and/or heterogeneous population of diltiazem pellets as described above are also within the scope of the present invention. The preparation of the diltiazem pellets are described in the above referenced patents which are incorporated herein by reference.

The diltiazem or a pharmaceutically acceptable salt thereof used in the present invention should be micronized and preferably have a particle size of less than 20 microns. The micronized diltiazem is used to prepare pellets or beads.

Various methods for preparing diltiazem pellets are known in the art such as extrusion spheronization and coating of inert starting seed. If inert starting seeds are employed the seed can be any type of commonly known starting material such as microcrystalline cellulose (CELLSPHERE®), glass, polypropylene, starch or sugar sphere having a diameter ranging from about 15-50 mesh and more preferably about 30-35 mesh.

The diltiazem is applied to the starting seed by spraying a solution or suspension containing the diltiazem and a binding agent. The binder employed in the active pellets can be any type of binding agent commonly known in the art such as polyvinyl pyrrolidone, hydroxyethylcellulose, hydroxypropyl cellulose, hydroxypropyl methylcellulose, polyacrylate, ethylcellulose or mixtures of the foregoing. In the preferred embodiment of the present invention, the binder for the active pellets is a combination of a water soluble binder, such as polyvinyl pyrrolidone or hydroxyethylcellulose and a water insoluble binder such as ethylcellulose or a polyacrylate. The ratio of water soluble binder to water insoluble binder should be about 1:1 to about 1:3 with the most preferred ratio being 1:2. These ratios are based upon the weight of the water soluble binder to the weight of the water insoluble binder in the active pellets.

The active pellets of the present invention will comprise the following ingredients:

| INGREDIENT | PREFERRED | MOST PREFERRED |
|---|---|---|
| diltiazem HCl | 50-85% | 65-80% |
| inert seed | 10-30% | 15-25% |
| binder | 1-15% | 4-10%. |

In a preferred embodiment of the present invention the active pellets will comprise the following ingredients:

| INGREDIENT | PREFERRED | MOST PREFERRED |
|---|---|---|
| diltiazem HCl | 50-85% | 65-80% |
| inert seed | 10-30% | 15-25% |
| water soluble binder | 0.25-5% | 1-3.4% |
| water insoluble binder | 0.75-10% | 3-6.6% |

All the percentages in the above tables are based on the total weight of the active pellets.

The active pellets of the present invention which comprise the diltiazem HCl is prepared by forming a suspension of the binder and drug, and then layering the suspension onto the inert seed using any of the layering techniques commonly known in the industry such as fluidized bed coating, rotary granulation or pan coating.

Once the active pellets are prepared, the active pellets can be coated with an extended release coating. The extended release coating is applied to the active pellets to control the release of the drug from the dosage form and preferably comprises a water insoluble water permeable polymer, a water or acid soluble channeling agent, a lubricating or dusting agent and optionally a surfactant.

Suitable water insoluble water permeable polymers are ethylcellulose, cellulose acetate and polyacrylates or mixtures thereof. In the preferred embodiment of the present invention, the water insoluble water permeable polymer is a polymethacrylate ester copolymer, such as a poly(ethylacrylate methylmethacrylate) copolymer which is commercially available from Rohm Pharma under the tradename EUDRAGIT NE 30D.

The channeling agent employed in the extended release coating can be any type of water or acid soluble pharmaceutically acceptable substance commonly known in the art such as polyvinyl pyrrolidone, hydroxyethylcellulose, hydroxypropyl cellulose, hydroxypropyl methylcellulose, polyacrylate, sucrose, drug itself or any combination of the foregoing. The preferred channeling agent is a water or acid soluble polymer such as hydroxypropyl methylcellulose.

Suitable lubricants or dusting agents that can be used in the present invention are talc, magnesium stearate, silicon dioxide, kaolin or a mixture of the foregoing. The lubricant or dusting agent prevents the pellets from sticking to one another during processing. The lubricant may be dusted onto the active pellets during the coating process or it may be incorporated into a coating suspension and applied to the core with the coating suspension. In a preferred embodiment of the present invention, the lubricant is a mixture of talc and magnesium stearate. The preferred ratio of talc to magnesium stearate should be about 1:2 to about 2:1. These ratios are based upon the weight of the talc to the weight of the magnesium stearate.

Suitable surfactants that may optionally be used in the present invention are sodium lauryl sulfate, sodium taurocholate or a polysorbate. The preferred surfactant is polysorbate 80.

The extended release coating can be applied to the active pellets by any means commonly known in the industry such as a rotary granulator, pan coater or a fluidized bed coater.

The extended release coating of the present invention will have the following composition:

| COATING: | Preferred | Most Preferred |
| --- | --- | --- |
| water insoluble polymer | 60-85% | 65-80% |
| channeling agent | 0.5-5% | 0.75-2% |
| lubricant | 10-40% | 15-30% |
| surfactant (optionally) | less than 1% | less than 0.5% |

In a preferred embodiment of the present invention the extended release coating will comprise the following ingredients:

| COATING: | Preferred | Most Preferred |
| --- | --- | --- |
| water insoluble polymer | 60-85% | 65-80% |
| channeling agent | 0.5-5% | 0.75-2% |
| talc | 5-20% | 7.5-15% |
| magnesium stearate | 5-20% | 7.5-15% |
| surfactant (optionally) | less than 1% | less than 0.5% |

The percentages listed in the above tables are based on the total weight of the extended release coating.

Generally, the extended release coating will comprise from about 1% to about 20%, preferably about 1.5% to about 15%, based on the total weight of the active pellet and extended release coating.

As mentioned above, the dosage form of the present invention may comprise a heterogeneous population of pellets wherein the dosage form comprises pellets with varying amounts or thicknesses of extended release coating applied to the active pellets. For example the heterogeneous population may comprise a mixture of homogeneous pellets as defined above and uncoated active pellets that provide an immediate release amount of the diltiazem. The heterogeneous population may also be formed by blending extended release pellets that are prepared with different amounts or thicknesses of extended release coating. The extended release pellets with varying thicknesses may be prepared in separate and distinct batches or by the single batch intermittent process of the present invention wherein multiple allotments of active pellets are added to a coating equipment at periodic time intervals during the coating process.

In a preferred embodiment of the present invention a heterogeneous population of extended release pellets are prepared in a single batch intermittent process using fluidized bed coating equipment wherein the population is prepared by adding three separate allotments of active pellets to the coating equipment during the coating process. The process comprises the steps of:

1) adding a first allotment of active pellets to the coating equipment;
2) coating the first allotment of active pellets with a first amount of extended release coating;
3) adding a second allotment of active pellets to the coating equipment;
4) coating the first and second allotment of active pellets with a second amount of extended release coating;
5) adding a third allotment of active pellets to the coating equipment; and
6) coating the first, second and third allotments of active pellets with a third amount of extended release coating.

A suitable heterogeneous population of diltiazem pellets useful in the present invention can be prepared wherein the amounts of the first, second and third allotments of active pellets added to the coating equipment are equal, however it is preferred that the active pellets be added to the coating equipment in the following proportions:

| Allotment | Preferred % | Most Preferred % |
| --- | --- | --- |
| first | 34-90% | 65-85% |
| second | 5-33% | 5-15% |
| third | 5-43% | 10-25% |

All the percentages in the above table are based on the total weight of the active pellets in the dosage formulation.

A suitable heterogeneous population of diltiazem pellets for use in the present invention can also be prepared according to the above described process wherein the quantity of the first, second and third amounts of extended release coating are equal, however, it is preferred that the quantities of the first, second and third amounts of extended release coating be as follows:

| Coating | Preferred % | Most Preferred % |
| --- | --- | --- |
| first | 10-33% | 15-25% |
| second | 34-80% | 50-75% |
| third | 10-40% | 15-30% |

All the percentages in the above table are based on the total weight of the extended release coating to be applied to the active pellets in the dosage formulation.

In the most preferred embodiment of the present invention, the extended release coating is applied to the active pellets with an atomization pressure of 2-5 bars, product temperature of 20-30° C., and a spray rate of: 100-600 g/min for the first amount of extended release coating; 200-1100 g/min for the second amount of extended release coating and 500-1100 g/min for the third amount of the extended release coating.

The diltiazem pellets of the present invention, either homogeneous or heterogeneous population of pellets, prior to mixing with the gel-forming material should exhibit the following dissolution profile when tested in a USP type 2 apparatus at 75 rpm in 900 ml of simulated intestinal fluid (pH 7.5 phosphate buffer) and at 37° C.:

| Time (hours) | Preferred | Most Preferred |
| --- | --- | --- |
| 2 | 0-30% | 5-25% |
| 4 | 10-50% | 15-45% |
| 8 | 30-85% | 45-80% |
| 12 | 45-90% | 60-85% |
| 16 | NLT 60% | NLT 70% |
| 20 | NLT 70% | NLT 75% |

NLT = NOT LESS THAN

The diltiazem pellets of the present invention, either homogeneous or heterogeneous population of pellets, prior to mixing with the gel-forming material should exhibit the following dissolution profile when tested in a USP type 2 apparatus at 75 rpms in 900 ml of simulated gastric fluid (SGF) and at 37° C.:

| Time (hours) | Preferred | Most Preferred |
| --- | --- | --- |
| 2 | 0-30% | 5-25% |
| 4 | 10-50% | 15-45% |
| 8 | 25-80% | 40-75% |
| 12 | 50-90% | 55-85% |
| 16 | NLT 55% | NLT 65% |
| 20 | NLT 65% | NLT 70% |

NLT = NOT LESS THAN

The diltiazem pellets of the present invention, either homogeneous or heterogeneous population of pellets, prior to mixing with the gel-forming material should exhibit the following dissolution profile when tested in a USP type 2 apparatus at 100 rpm in 900 ml of 0.1 N HCl and at 37° C.:

| Time (hours) | Preferred | Most Preferred |
| --- | --- | --- |
| 2 | 0-30% | 5-25% |
| 4 | 5-45% | 10-35% |
| 8 | 20-70% | 35-65% |
| 12 | NLT 45% | NLT 50% |
| 18 | NLT 55% | NLT 60% |
| 20 | NLT 65% | NLT 70% |

NLT = NOT LESS THAN

Once the diltiazem pellets are prepared, they are mixed with a gel-forming material, a lubricant and optionally other conventional excipients such as a flux enhancer, filler, a disintegrant, a flow aid, or combinations of the foregoing so that the $T_{max}$ of the final dosage form is achieved 8 hours or more after administration, preferably 10 hours or more after administration, more preferably between 10 and 15 hours after administration and most preferably between 10 and 13 hours after administration. It will be understood that one excipient may exhibit more than one function in the formulation. For example, microcrystalline cellulose may act as a disintegrant, flow aid and filler depending upon the amount and manner in which the material is employed. These dual and multi function excipients are well known to those skilled in the art.

The final dosage form of the present invention will preferably have the following composition:

| | Preferred | Most Preferred |
| --- | --- | --- |
| Diltiazem Pellets | 35-85% | 45-75% |
| Gel-Forming Material | 1.0-40% | 5.0-25% |
| Lubricant | 0.1-10% | 0.5-5.0% |
| Flux Enhancer | 0.0-25% | 0.0-15% |
| Flow Aid | 0.0-20% | 0.0-15% |
| Filler | 0.0-40% | 10-35% |
| Disintegrant | 0.0-40% | 10-35% |

The diltiazem pellets, gel-forming material and conventional processing excipients can be mixed together using conventional techniques known in the art. Once the diltiazem pellets, gel-forming material, and other conventional processing excipients are mixed together, the mixture can be tableted using conventional tableting techniques such as a rotary tablet press or filled into gelatin capsules. The final dosage form, especially in tablet form, can be further coated with a water soluble seal coat, aesthetic or color coat and polished with a wax coating. In addition as mentioned above, if desired, a coating of diltiazem can be applied to the outer surface of the final dosage form to provide an immediate release amount of diltiazem.

The final dosage form of the present invention should exhibit the following dissolution profile when tested in a USP type 1 apparatus at 100 rpm in 900 ml of simulated intestinal fluid (pH 7.5 phosphate buffer) and at 37° C.:

| Time (hours) | Preferred | Most Preferred |
| --- | --- | --- |
| 1 | 0-30% | 0-20% |
| 4 | 0-40% | 0-30% |
| 12 | NLT 30% | NLT 40% |
| 24 | NLT 60% | NLT 70% |

NLT = NOT LESS THAN

The following examples illustrate the present invention and are not intended to limit the scope of the present invention.

Example 1

A dosage form containing a heterogeneous population of pellets was prepared by forming active pellets having the following composition:

| STEP I: ACTIVE PELLET | |
| --- | --- |
| Ingredient | Weight % |
| diltiazem HCl, USP (micronized)[1] | 75.00% |
| sugar sphere, NF[2] | 18.18% |
| ethylcellulose, NF (ETHOCEL 10 cps) | 4.56% |
| povidone, USP (K-30) | 2.27% |

[1] average particle size of less than 20 microns.
[2] 30/35 mesh.

The active core was prepared by adding 25.08 kg of the ethylcellulose to 836.0 kg of isopropyl alcohol while mixing with a tri-blender and homogenizing for about 30 minutes. Once the ethylcellulose was dissolved, 12.49 kg of povidone was added to the ethylcellulose solution and homogenized for an additional 10 minutes. After the ethylcellulose and povidone were dissolved, 412.6 kg of diltiazem was added scoopwise to the ethylcellulose/povidone solution while mixing until a uniform suspension was obtained. The diltiazem suspension was then applied to 100.0 kg of the sugar spheres in a fluidized bed coater (GLATT GPCG 200) under the following conditions: product temperature: 25-30° C. (target of 27° C.); atomization pressure: 2-3.5 bars; air volume of 800-3200 CFM and a pump rate as follows:

| Time (min.) | Target Spray Rate (g/min) |
|---|---|
| 0-45 | 597-802 |
| 46-75 | 800-1203 |
| 76-105 | 1197-1705 |
| 106-135 | 1700-2300 |
| 136-255 | 2299-2802 |
| 256-end | 2796-3060 |

Once the diltiazem suspension was consumed, the inlet temperature was increased to 70° C. and the active pellets were dried in the fluidized bed coater for approximately 10 minutes or until the LOD (loss on drying) was less than 2%. Once the drying stage was completed, the dried diltiazem active pellets are sieved and placed in a clean, properly labeled double polyethylene bag lined container.

The active pellets sized between 14 and 24 mesh were coated with an extended release coating in a single batch intermittent coating process to form a heterogeneous population of pellets wherein the extended release coating had the following composition:

| STEP II: Extended Release Coating | |
|---|---|
| Ingredient | Weight % |
| Eudragit NE 30D[1], EP | 73.67% |
| hydroxypropyl methylcellulose, USP (Methocel E5) | 1.00% |
| talc, USP (I) | 12.58% |
| magnesium stearate, NF | 12.58% |
| polysorbate 80, NF | 0.17% |

[1]30% aqueous dispersion

The controlled release coating was prepared by adding 0.256 kg of the Methocel E5 Premium to 32.24 kg of purified water, USP, and mixing with a mechanical stirrer for approximately 60 minutes. After mixing, the solution was allowed to sit for about 20 minutes to defoam. 3.227 kg of talc was added to the Methocel E5/water mixture while mixing.

In a separate container, 0.0436 kg of polysorbate 80 was added to 9.54 kg of isopropyl alcohol and mixed with a mechanical mixer for approximately 2 minutes. 3.227 kg of magnesium stearate was added to the polysorbate 80/isopropyl alcohol mixture and the mixing continued for approximately 5 minutes.

Once the magnesium stearate had been mixed, the Methocel E5 and talc mixture was added to the magnesium stearate/polysorbate 80 mixture. The resulting composition was mixed for about 3 minutes.

After gently shaking, 62.97 kg of Eudragit NE 30D was weighed and filtered through an 80 mesh stainless steel screen. The mixture of Methocel E5, talc, magnesium stearate, polysorbate 80 was added to the Eudragit NE 30D and mixed with a mechanical mixer for at least ten minutes before applying the resulting extended release coating suspension to the active pellets using a fluidized bed coater (GLATT GPCG-60). Stirring of the extended release coating continued throughout the coating process.

The extended release coating suspension with the above composition was applied to the active pellets by adding 164.53 kg of a first allotment of active pellets to the fluidized bed coater and preheating the first allotment of active pellets for two minutes with an inlet temperature 40° C. The extended release coating suspension is applied to the first allotment of active pellets under the following conditions: product temperature: 25-27° C. (target 25° C.); atomization pressure: 3 bars; and a pump rate of 450 g/min (range 400-500). After approximately 18.58 kg±0.1 kg of extended release coating suspension was applied to the first allotment of active pellets, the coated active pellets were cooled in the coater until the air inlet temperature reached approximately 25° C.

Once the first allotment of active pellets were cooled, approximately 21.37 kg of a second allotment of active pellets were added to the coater. The first and second allotment of active pellets were then coated with approximately 65.02 kg±0.1 kg of extended release coating suspension under the following conditions: product temperature: 25-27° C. (target 25° C.); atomization pressure: 3 bars; and a pump rate of 550 g/min (range 500-600). After the 65.02 kg of extended release coating suspension was applied to the first and second allotment of active pellets, the coated first and second allotment of active pellets were cooled in the coater until the air inlet temperature reached approximately 25° C.

After the coated first and second allotment of active pellets were cooled, approximately 38.46 kg of a third allotment of active pellets were added to the coater. The first, second and third allotment of active pellets were then coated with the remaining amount of the extended release coating suspension under the following conditions: product temperature: 25-27° C. (target 25° C.); atomization pressure: 3 bars; and a pump rate of 950 g/min (range 900-1000) product temperature. After all the extended release coating suspension was consumed, the air inlet temperature was increased to 35° C. the first, second and third coated allotments of active pellets were dried in the fluidized bed coater to a product temperature of 32° C. Drying continued until the LOD was less than 2%. Thereafter the coated pellets were dusted with 5.00 kg of talc, dried in an oven for 40 hours at 60° C. and sieved using a sieve equipped with 12 mesh and 24 mesh screens. The heterogeneous populations of extended release diltiazem pellets was then compressed into tablets with the following composition:

| STEP III: Extended Release Tablets | |
|---|---|
| Ingredient | Weight % |
| Extended Release Pellets (Step II) | 52.25% |
| Confectioner's Sugar | 6.50% |
| Polyethylene Oxide | 20.00% |
| Magnesium Stearate, NF | 1.00% |
| Microcrystalline Cellulose, NF | 20.25% |

The extended release tablets were prepared by screening and mixing 1.625 kg of confectioner's sugar, NF (6× micronized), 5.0 kg of polyethylene oxide, NF, (10-20 mesh tablet grade POLYOX WSR N-80) and 5.063 kg of microcrystalline cellulose (Avicel PH 101) in a V-blender for about 10 minutes. After blending for about 10 minutes, 13.06 kg of the heterogeneous population of extended release diltiazem pellets prepared in Step II above were added to the V-blender and blended for about 15 minutes. 0.25 kg of magnesium stearate was then added to the V-blender and blended for an additional 5 minutes.

The mixture was then compressed into tablets containing approximately 420 mg of diltiazem using a Fette tablet press. The resulting tablets were standard concave capsule shape with a target weight of 1,200 mg and a hardness of 8-20 kp (target 14 kp). 19.20 kg of the tablets were then coated with a seal coat of 0.4867 kg of OPADRY II WHITE Y-30-18037 and polished with 0.0096 kg of candelilla wax using a pan coater.

The resulting tablets were tested in simulated intestinal fluid (pH 7.5 phosphate buffer), according to the procedure described in United States Pharmacopoeia 25, using Apparatus 1, basket @ 100 rpm. The results of the in vitro tests were as follows:

| TIME | % RELEASED |
|---|---|
| 1 | 1 |
| 2 | 3 |
| 4 | 9 |
| 8 | 30 |
| 12 | 55 |
| 16 | 69 |
| 24 | 78 |

The release profile of the extended release tablet prepared in this Example is shown in FIG. 1.

Figure 3:
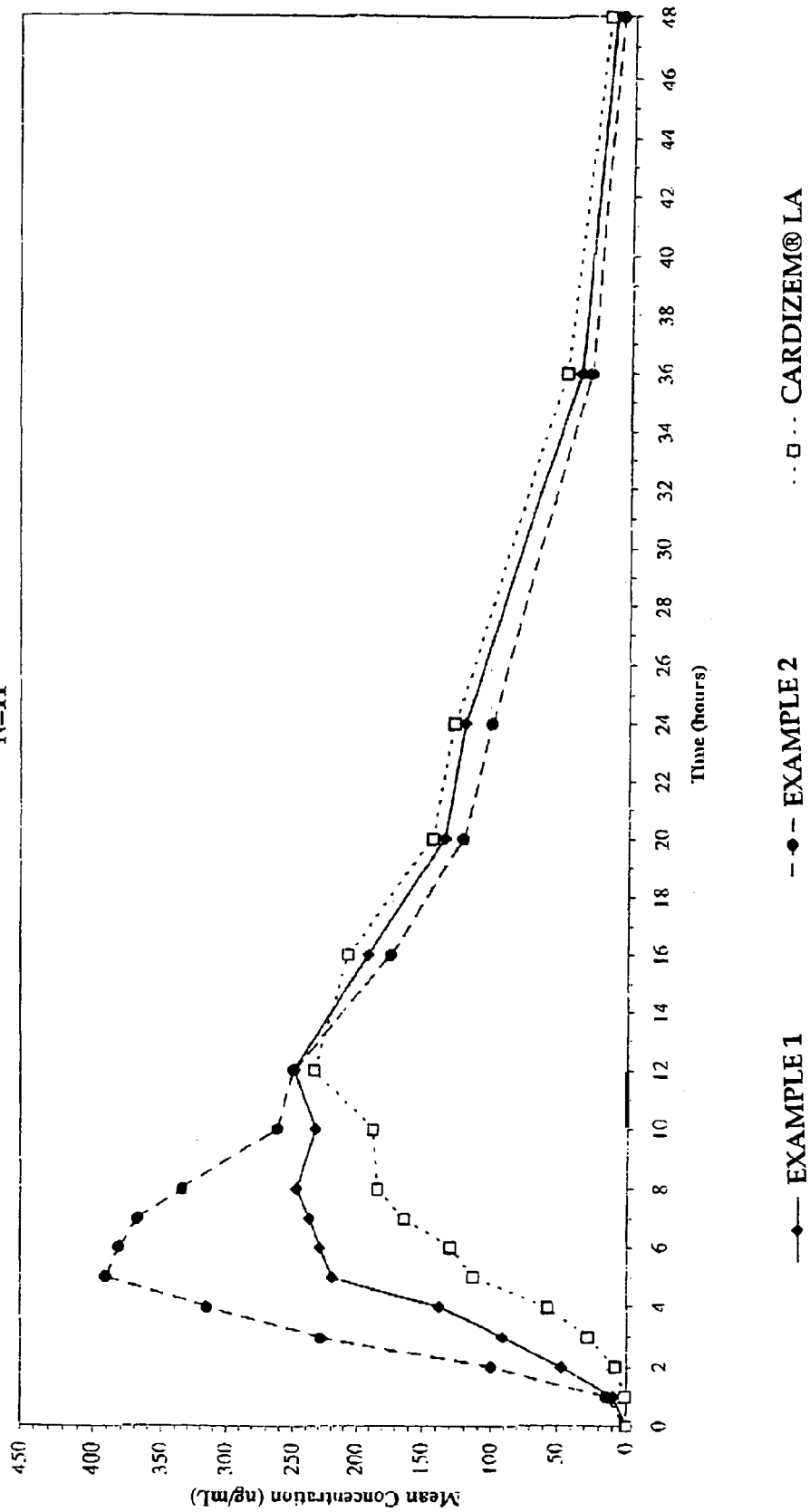
FIG. 3 is a graph depicting the linear plot of the mean plasma diltiazem concentration verses time of the formulation described in Examples 1 and 2 under fasting conditions and the linear plot of the mean plasma diltiazem concentration verses time of the commercially available diltiazem product CARDIZEM® La under fasting conditions with N=11.

Table 1 is a summary of the bioavailability comparison data under fasting conditions, test/reference ratio, shown in FIG. 3 wherein the test product was prepared according to Example 1 and the CARDIZEM® LA product is the reference product in a two way crossover biostudy with n=11.

TABLE 1

|  | Test Mean | Ref Mean | Test/Ref Ratio |
|---|---|---|---|
| $C_{max}$(ng/ml) | 289.69 | 253.88 | 114.10 |
| $AUC_{inf}$(ng · hr/ml) | 5503.47 | 5166.66 | 106.52 |
| $T_{max}$(hr) | 9.05 | 12.41 | 72.93 |
|  | Test G. Mean | Ref. G. Mean | G Mean Ratio |
| $C_{max}$(ng/ml) | 258.09 | 226.99 | 113.70 |
| $AUC_{inf}$(ng · hr/ml) | 4758.77 | 4617.46 | 103.06 |

Example 2

An extended release tablet containing a heterogeneous population of diltiazem pellets was prepared as described in Example 1 except the tablet comprises the following ingredients:

| STEP III: Extended Release Tablets | | |
|---|---|---|
| Ingredient | Weight % | Amount (kg) |
| Extended Release Pellets (Step II) | 52.25% | 13.060 kg |
| Confectioner's Sugar | 5.00% | 1.250 kg |
| Compressible sugars | 6.50% | 1.625 kg |
| Polyethylene Oxide | 10.00% | 2.500 kg |
| Magnesium stearate, NF | 1.00% | 0.250 kg |
| Microcrystalline Cellulose, NF | 25.25% | 6.313 kg |

19.20 kg of the tablets were then coated with a seal coat of 0.4867 kg of OPADRY II WHITE Y-30-18037 and polished with 0.0096 kg of candelilla wax using a pan coater.

The resulting tablets were tested in simulated intestinal fluid (pH 7.5 phosphate buffer), according to the procedure described in United States Pharmacopoeia 25, using Apparatus 1, basket @ 100 rpm. The results of the in vitro tests were as follows:

| TIME | % RELEASED |
|---|---|
| 1 | 2 |
| 2 | 6 |
| 4 | 24 |
| 8 | 60 |
| 12 | 76 |
| 16 | 82 |
| 24 | 88 |

Figure 2:
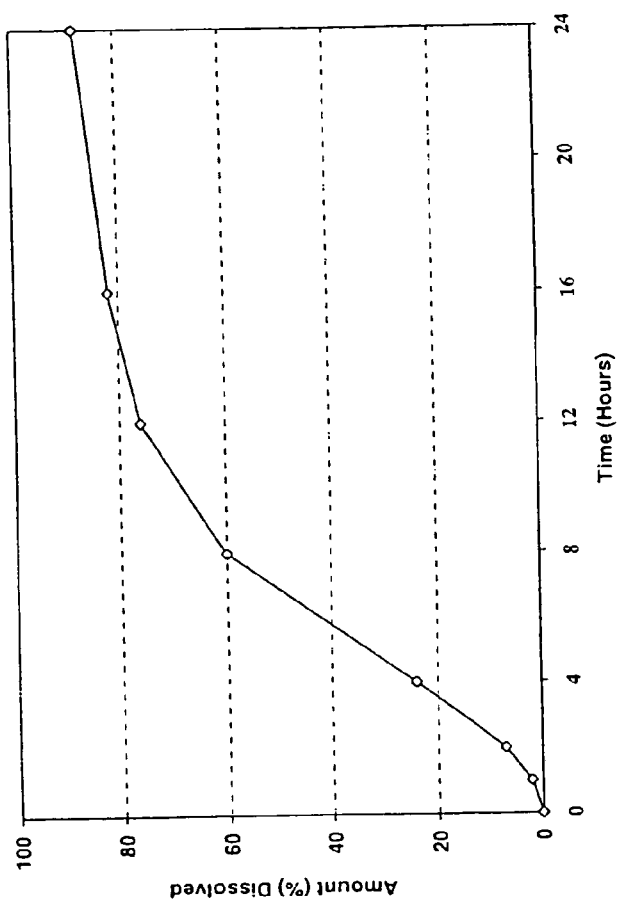
FIG. 2 is a graph depicting the dissolution profile in simulated intestinal fluid (pH 7.5 phosphate buffer), of the formulation described in Example 2 as tested according to the procedure described in United States Pharmacopoeia 25, Apparatus 1 @ 100 rpm.

The release profile of the extended release tablet prepared in this Example is shown in FIG. 2.

Table 2 is a summary of the bioavailability comparison data under fasting conditions, test/reference ratio, shown in FIG. 3 wherein the test product was prepared according to Example 2 and the CARDIZEM® LA product is the reference product in a two way crossover biostudy with n=11.

TABLE 2

|  | Test Mean | Ref Mean | Test/Ref Ratio |
|---|---|---|---|
| $C_{max}$(ng/ml) | 410.34 | 253.88 | 161.63 |
| $AUC_{inf}$(ng · hr/ml) | 6032.37 | 5166.66 | 116.76 |
| $T_{max}$(hr) | 5.82 | 12.41 | 46.87 |
|  | Test G. Mean | Ref. G. Mean | G Mean Ratio |
| $C_{max}$(ng/ml) | 345.35 | 226.99 | 152.14 |
| $AUC_{inf}$(ng · hr/ml) | 4966.84 | 4617.46 | 107.57 |

Example 3

An extended release tablet containing a heterogeneous population of diltiazem pellets was prepared as described in Example 1 except the tablet comprises the following ingredients:

| STEP III: Extended Release Tablets | | |
|---|---|---|
| Ingredient | Weight % | Amount (kg) |
| Extended Release Pellets (Step II) | 52.25% | 73.15 kg |
| Polyethylene Oxide | 24.75% | 34.65 kg |
| Microcrystalline Cellulose, NF | 21.75% | 30.45 kg |
| Magnesium stearate, NF | 1.00% | 1.40 kg |
| Colloidal Silicon Dioxide | 0.25% | 0.35 kg |

129.12 kg of the tablets were then coated with a seal coat of 3.529 kg of OPADRY II WHITE Y-30-18037 and polished with 0.00696 kg of candelilla wax using a pan coater.

The resulting tablets were tested in simulated intestinal fluid (pH 5.8 phosphate buffer), Apparatus II, (paddles) @ 100 rpm in 900 ml dissolution volume. The results of the in vitro tests were as follows:

| TIME | % RELEASED |
|---|---|
| 2 | 7 |
| 6 | 36 |
| 8 | 56 |
| 14 | 89 |
| 24 | 100 |

Figure 4:
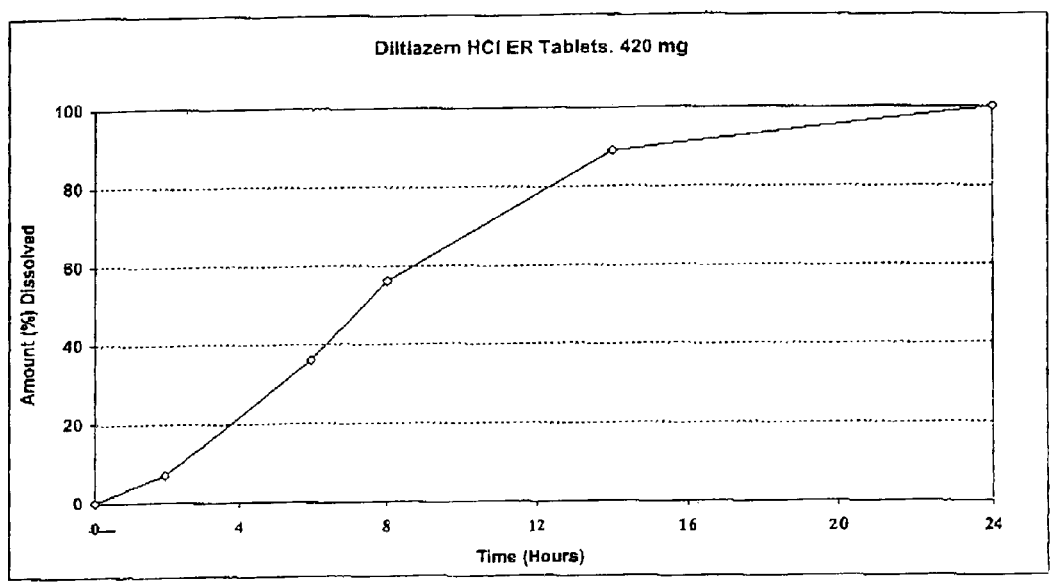
FIG. 4 is a graph depicting the dissolution profile in simulated intestinal fluid (pH 5.8 phosphate buffer), of Example 3 as tested in Apparatus II (paddle) @ 100 rpm in 900 ml dissolution volume.

The release profile of the extended release tablet prepared in this Example is shown in FIG. 4.

A bioavailability study of the test diltiazem hydrochloride extended release tablets 420 mg prepared according to Example 3 was compared to the reference CARDIZEM® La Tablets 420 mg in forty eight healthy subjects (22 males, 26 females) under fasting conditions using a randomized, single-dose, two-treatment, two-sequence, four-period, replicate design.

Figure 5:
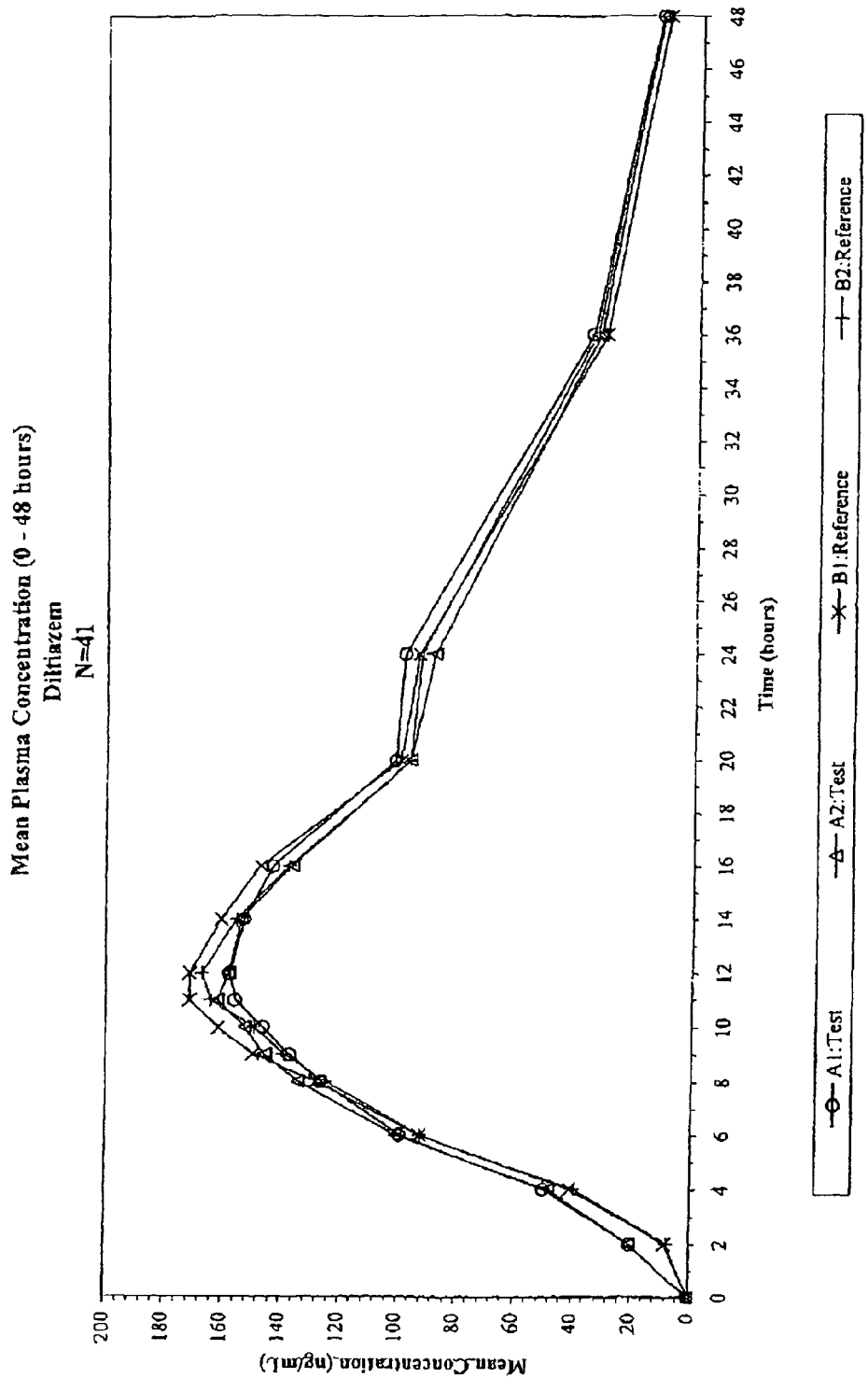
FIG. 5 is a graph depicting the linear plot of the mean plasma diltiazem concentration verses time of the formulation described in Example 3 under fasting conditions and the linear plot of the mean plasma diltiazem concentration verses time of the commercially available diltiazem product CARDIZEM® La under fasting conditions with 41 patients (A1 and A2 and B1 and B2 refer to the two-treatment, two-sequence, nature of the clinical trials).

Table 4 is a summary of the bioavailability comparison data under fasting conditions, test/reference ratio, shown in FIG. 5, wherein the test product was prepared according to Example 3 and the CARDIZEM® LA product is the reference product in a two way crossover biostudy with n=41.

TABLE 4

|  | Test Mean | Ref Mean | Test/Ref Ratio |
| --- | --- | --- | --- |
| $C_{max}$(ng/ml) | 181.38 | 190.57 | 95.18 |
| $AUC_{inf}$(ng · hr/ml) | 3761.38 | 3711.10 | 101.35 |
| $T_{max}$(hr) | 11.93 | 11.93 | 100.02 |
|  | Test G. Mean | Ref. G. Mean | G Mean Ratio |
| $C_{max}$(ng/ml) | 167.24 | 169.68 | 98.56 |
| $AUC_{inf}$(ng · hr/ml) | 3493.65 | 3409.92 | 102.46 |

Figure 6:
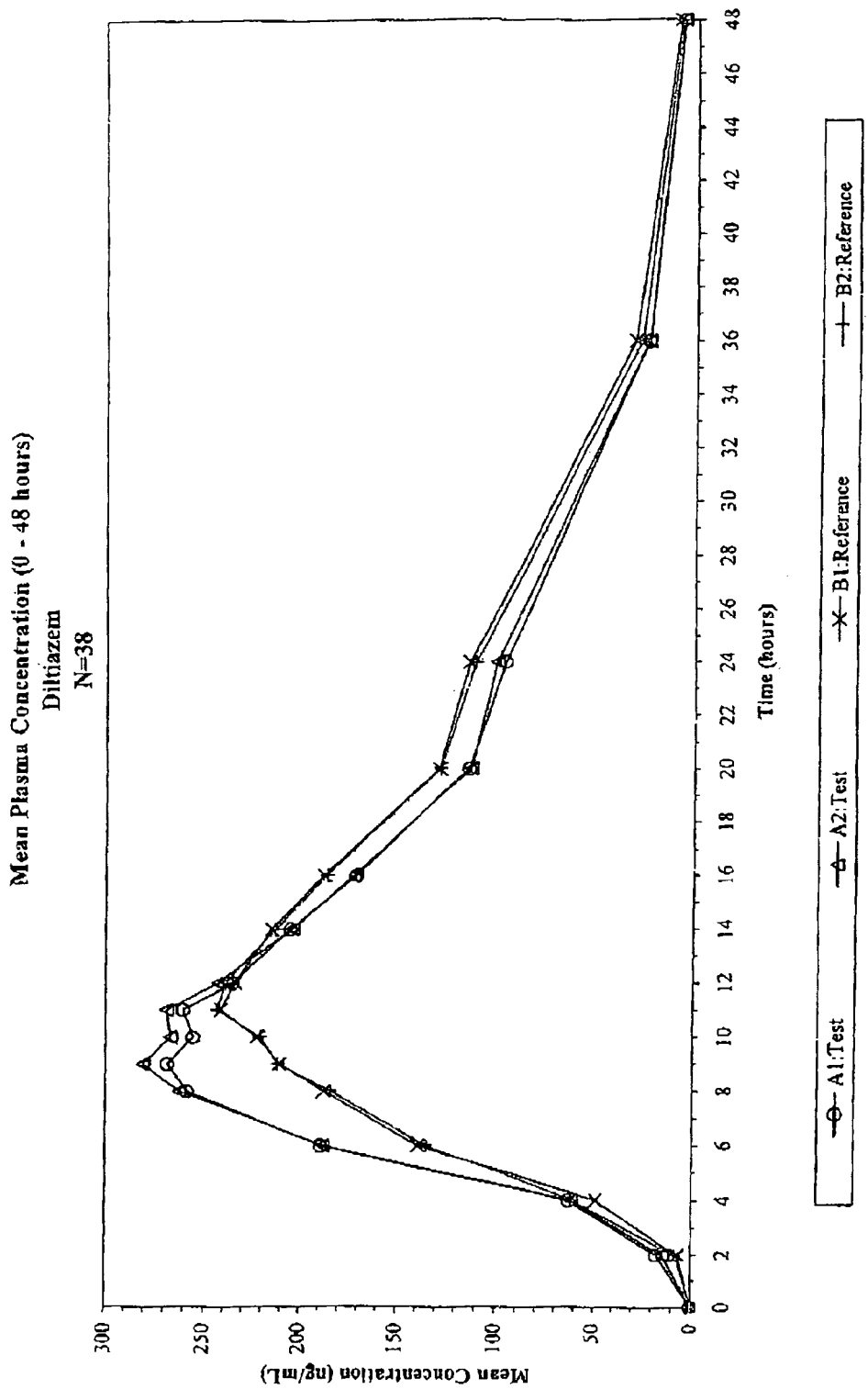
FIG. 6 is a graph depicting the linear plot of the mean plasma diltiazem concentration verses time of the formulation described in Example 3 under non-fasting conditions and the linear plot of the mean plasma diltiazem concentration verses time of the commercially available diltiazem product CARDIZEM® La under non-fasting conditions with 38 patients (A1 and A2 and B1 and B2 refer to the two-treatment, two-sequence, nature of the clinical trials).

Table 6 is a summary of the bioavailability comparison data under non-fasting conditions, test/reference ratio, as shown in FIG. 6 wherein the test product was prepared according to Example 3 and CARDIZEM LA product is the reference product in a two way crossover biostudy with n=38.

TABLE 6

|  | Test Mean | Ref Mean | Test/Ref Ratio |
| --- | --- | --- | --- |
| $C_{max}$(ng/ml) | 302.46 | 257.50 | 117.46 |
| $AUC_{inf}$(ng · hr/ml) | 4691.30 | 4629.85 | 101.63 |
| $T_{max}$(hr) | 9.60 | 10.84 | 88.50 |
|  | Test G. Mean | Ref. G. Mean | G Mean Ratio |
| $C_{max}$(ng/ml) | 289.96 | 243.17 | 119.24 |
| $AUC_{inf}$(ng · hr/ml) | 4487.96 | 4372.85 | 102.63 |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release oral pharmaceutical formulation comprising a tablet consisting of a mixture of (A) extended release diltiazem pellets, and (B) a gel-forming material,
   wherein (A) consists of:
   45-75% of the total weight of the tablet and is a heterogeneous population of extended release diltiazem pellets wherein the extended release diltiazem pellets comprise:
      i) a pellet core comprising diltiazem; and
      ii) an extended release coating applied to the pellet core wherein the extended release coating controls the release of the drug from the pellet core so that the heterogeneous population of pellets exhibits a dissolution profile when tested in a USP Type 2 apparatus at 75 rpms, and 900 ml of simulated intestinal fluid (pH 7.5 phosphate buffer) at 37° C.:
         0-30% of the diltiazem is released after 2 hours;
         10-50% of the diltiazem is released after 4 hours;
         30-85% of the diltiazem is released after 8 hours;
         45-90% of the diltiazem is released after 12 hours;
         not less than 60% of the diltiazem is released after 16 hours;
         and not less than 70% of the diltiazem released after 20 hours;
   and (B) consists of:
      (i) a polymer that can retain a fraction of imbibed fluid and exhibit a 2 to 50 fold volume increase selected from the group consisting of polyhydroxyalkylcellulose having a molecular weight greater than 50,000, poly(hydroxyalkylmethacrylate) having a molecular weight of from 5,000 to 5,0000,000, an acrylic acid polymer, a polymer of acrylic acid cross-linked with a polyalkyl ether of sucrose, and polyethylene oxide having a molecular weight of 100,000 to 5,000,000; and
      (ii) conventional processing excipients selected from fillers, lubricants, glidants, pigments, polishing agents and combinations of the foregoing;
   wherein the mixture of (A) and (B) is compressed into a tablet and the combination of the extended release coating on the extended release pellets and the polymer of the gel-forming material controls the release of the diltiazem from the tablet so the time of maximum blood plasma diltiazem concentration occurs about 10 to about 15 hours after administration of the tablet;
   and wherein the tablet exhibits a dissolution profile when tested in a USP Type 1 apparatus at 100 rpms, and 900 ml of simulated intestinal fluid (pH 7.5 phosphate buffer) at 37° C.:
      0-30% of the diltiazem is released after 1 hour;
      0-40% of the diltiazem is released after 4 hours;
      not less than 30% of the diltiazem is released after 12 hours; and
      not less than 60% of the diltiazem is released after 24 hours;
   and wherein the polymer of the gel-forming material is 5-25% of the total weight of the tablet and the gel-forming material is free of flux enhancers selected from the group consisting of magnesium sulfate, magnesium chloride, sodium chloride, potassium chloride, lithium chloride, potassium sulfate, sodium carbonate, sodium sulfate, lithium sulfate, potassium acid phosphate, calcium lactate, tartaric acid, lactose, fructose, sucrose, mannitol, sorbitol and mixtures thereof and the tablet may optionally be coated with a water soluble seal coat, aesthetic coat, color coat or polishing coat.

2. The formulation as defined in claim 1 wherein the time of maximum blood plasma diltiazem concentration occurs between 10 and 13 hours after administration of the formulation.

3. The formulation of claim 1 wherein the heterogeneous population of extended release pellets prior to mixing with the gel-forming material exhibits the following dissolution profile when tested in a USP Type 2 apparatus at 75 rpms, and 900 ml of simulated intestinal fluid (pH 7.5 phosphate buffer) at 37° C.:
   5-25% of the diltiazem is released after 2 hours;
   15-45% of the diltiazem is released after 4 hours;
   45-80% of the diltiazem is released after 8 hours;
   60-85% of the diltiazem is released after 12 hours;
   not less than 70% of the diltiazem is released after 16 hours; and
   not less than 75% of the diltiazem released after 20 hours;
and the tablet exhibits the following dissolution profile tested in a USP Type 1 apparatus at 100 rpms, and 900 ml of simulated intestinal fluid (pH 7.5 phosphate buffer) at 37° C.:
   0-20% of the diltiazem is released after 1 hour;
   0-30% of the diltiazem is released after 4 hours;

not less than 40% of the diltiazem is released after 12 hours; and not less than 70% of the diltiazem is released after 24 hours.

4. The formulation as described in claim 1 wherein the polymer of the gel-forming material is polyethylene oxide.

5. A controlled release oral pharmaceutical formulation comprising a tablet consisting of a mixture of (A) extended release diltiazem pellets, (B) polyethylene oxide, and (C) conventional processing excipients, wherein (A) consists of:
45-75% of the total weight of the tablet of a heterogeneous population of extended release diltiazem pellets wherein the extended release diltiazem pellets comprise: i) a core comprising diltiazem and ii) an extended release coating applied to the core wherein the extended release coating controls the release of the diltiazem from the core so that the heterogeneous population of pellets exhibits the following dissolution profile when tested in a USP Type 2 apparatus at 75 rpms, and 900 ml of simulated intestinal fluid (pH 7.5 phosphate buffer) at 37° C.:
 0-30% of the diltiazem is released after 2 hours;
 10-50% of the diltiazem is released after 4 hours;
 30-85% of the diltiazem is released after 8 hours;
 45-90% of the diltiazem is released after 12 hours;
 not less than 60% of the diltiazem is released after 16 hours; and
 not less than 70% of the diltiazem released after 20 hours;

(B) consists of:
5-25% of the total weight of the tablet of a polyethylene oxide having a molecular weight of 100,000 to 5,000,000;

and (C) consists of:
conventional processing excipients selected from fillers, lubricants, glidants, pigments, polishing agents and combinations of the foregoing wherein the mixture of (A), (B) and (C) is compressed into a tablet, and the combination of the extended release coating on the extended release pellets and polyethylene oxide controls the release of the diltiazem from the tablet so the time of maximum blood plasma diltiazem concentration occurs about 10 to about 15 hours after administration of the tablet, the tablet exhibits the following dissolution profile when tested in a USP Type 1 apparatus at 100 rpms, and 900 ml of simulated intestinal fluid (pH 7.5 phosphate buffer) at 37° C.:
 0-30% of the diltiazem is released after 1 hour;
 0-40% of the diltiazem is released after 4 hours;
 not less than 30% of the diltiazem is released after 12 hours; and
 not less than 60% of the diltiazem is released after 24 hours;

and wherein the polyethylene oxide is 1-40% of the total weight of the tablet and the polyethylene oxide and conventional processing excipients mixed with the extended release diltiazem pellets is free of flux enhancers selected from the group consisting of magnesium sulfate, magnesium chloride, sodium chloride, potassium chloride, lithium chloride, potassium sulfate, sodium carbonate, sodium sulfate, lithium sulfate, potassium acid phosphate, calcium lactate, tartaric acid, lactose, fructose, sucrose, mannitol, sorbitol and mixtures thereof and the tablet may optionally be coated with a water soluble seal coat, aesthetic coat, color coat or polishing coat.

* * * * *